United States Patent
Duan et al.

(10) Patent No.: US 11,399,810 B2
(45) Date of Patent: *Aug. 2, 2022

(54) MAGNETICALLY CONTROLLED DIGESTIVE TRACT LIQUID COLLECTION SYSTEM AND CAPSULE

(71) Applicant: Ankon Medical Technologies (Shanghai) Co., LTD., Shanghai (CN)

(72) Inventors: Xiaodong Duan, Pleasanton, CA (US); Shaobang Zhang, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 870 days.

This patent is subject to a terminal disclaimer.

(21) Appl. No.: 16/248,804

(22) Filed: Jan. 16, 2019

(65) Prior Publication Data
US 2019/0216443 A1   Jul. 18, 2019

(51) Int. Cl.
*A61B 10/00*   (2006.01)
*A61B 5/06*   (2006.01)
(Continued)

(52) U.S. Cl.
CPC ........ *A61B 10/0045* (2013.01); *A61B 5/0031* (2013.01); *A61B 5/062* (2013.01);
(Continued)

(58) Field of Classification Search
CPC ... A61B 10/0045; A61B 5/0031; A61B 5/062; A61B 5/14539; A61B 5/14865; A61B 2010/0061; A61B 5/073; A61B 5/6861; A61B 5/7285; A61B 2010/061; A61B 5/07

See application file for complete search history.

(56) References Cited

U.S. PATENT DOCUMENTS

| 11,125,733 B2 * | 9/2021 | Duan .................. A61B 5/07 |
| 2013/0137921 A1 * | 5/2013 | Angot ................ A61B 1/041 600/109 |

(Continued)

FOREIGN PATENT DOCUMENTS

| CN | 101282677 A | * 10/2008 | ......... A61B 1/00082 |
| CN | 201719267 U | * 1/2011 | |

(Continued)

*Primary Examiner* — David J. McCrosky
*Assistant Examiner* — Reilly A Carlton
(74) *Attorney, Agent, or Firm* — Treasure IP Group, LLC (57) ABSTRACT

A magnetically controlled digestive tract liquid collection system and a capsule are provided. In an assembled state, with the constraint of a limit structure formed by a rotation limiting pin on an inner shell of the capsule and a rotation limiting slot in an outer shell of the capsule, and an angle exists between the N-S directions of a first magnetic cylinder and a second magnetic cylinder, a torque is present between the two magnetic cylinders, which makes parts inside the capsule tightly coupled. When an external magnetic field is applied, at least one or both of the two magnetic cylinders rotate under the action of the external magnetic field. When the external magnetic field is applied, the liquid inlets are in opened state, and when the external magnetic field is removed, the liquid inlets are in closed state.

18 Claims, 7 Drawing Sheets

(51) Int. Cl.
*A61B 5/145* (2006.01)
*A61B 5/1486* (2006.01)
*A61B 5/00* (2006.01)

(52) U.S. Cl.
CPC ...... *A61B 5/14539* (2013.01); *A61B 5/14865* (2013.01); *A61B 2010/0061* (2013.01)

(56) References Cited

U.S. PATENT DOCUMENTS

| | | | | |
|---|---|---|---|---|
| 2015/0065379 | A1* | 3/2015 | Sanyal | A61B 10/0045 600/580 |
| 2016/0310357 | A1* | 10/2016 | Duan | A61N 2/12 |
| 2017/0296425 | A1* | 10/2017 | Duan | A61F 5/0073 |
| 2017/0296428 | A1* | 10/2017 | Duan | A61H 23/0254 |
| 2018/0064425 | A1* | 3/2018 | Sanyal | A61B 10/0045 |
| 2019/0216443 | A1* | 7/2019 | Duan | A61B 5/073 |

FOREIGN PATENT DOCUMENTS

| | | | | |
|---|---|---|---|---|
| CN | 106796212 A | * | 5/2017 | A61B 10/0045 |
| CN | 109330634 A | * | 2/2019 | A61B 1/041 |
| CN | 109963499 A | * | 7/2019 | A61B 5/07 |
| WO | WO-2017024360 A1 | * | 2/2017 | A61B 10/0045 |
| WO | WO-2017117142 A1 | * | 7/2017 | A61B 10/0045 |

* cited by examiner

MAGNETICALLY CONTROLLED DIGESTIVE TRACT LIQUID COLLECTION SYSTEM AND CAPSULE

CROSS REFERENCE TO RELATED APPLICATIONS

This application claims priority to Chinese Patent Application No. 201810039617.2 filed on Jan. 16, 2018, the contents of which are incorporated by reference herein.

TECHNICAL FIELD

The invention relates to the technical field of a medical apparatus/system, specifically refers to a magnetically controlled digestive tract liquid collection system and a capsule.

BACKGROUND OF THE INVENTION

Because of the accelerated pace of work and uneven diet, modern people are exposed to an increasing incidence of digestive tract diseases which have become common in affecting the health of modern people, and are developing towards young people and hard-to-find positions. The detection of digestive tract diseases plays an important role. However, with a total length of over 9 meters, the human digestive tract in the shape of long and thin tube is distributed between various organs of the human body and shows an irregular and sealed structure which poses huge challenges to detection and sampling for upper gastrointestinal diseases.

To this end, the capsule for diagnosis and treatment of digestive tract conditions has been an important development direction in recent years. In view of the particularity of digestive tract, capsule miniaturization is a goal of the industry. Existing digestive tract capsules include a drive mechanism that is a core component of the capsule and generally integrated into the capsule shell. To a great extent, the degree of miniaturization of the capsule is determined by drive modes of the drive mechanism. The existing drive modes mainly include: motor drive, electromagnetic drive, compression spring drive, etc., or opening the capsule hole by these modes. Since the drive mechanism is integrated in the capsule, in view of the miniature size of the capsule itself, after integrating a drive mechanism, the capsule structure will become complicated, with low reliability and small capacity.

Therefore, it is necessary to propose a magnetically controlled digestive tract liquid collection system and a capsule, to simplify the capsule structure and to increase the capsule capacity under a certain capsule size limit.

SUMMARY OF THE INVENTION

The present invention discloses a capsule comprising an inner shell, an outer shell, a first magnetic cylinder, a second magnetic cylinder and an absorption medium, wherein the outer shell is larger than the inner shell, and the outer shell and the inner shell are matched with each other and are rotationally sealed; wherein the first magnetic cylinder is fixed in the inner shell, and the outer diameter of the first magnetic cylinder is matched with the inner diameter of the inner shell; wherein the second magnetic cylinder is fixed in the outer shell, and the outer diameter of the second magnetic cylinder is matched with the inner diameter of the outer shell; wherein the first magnetic cylinder and the second magnetic cylinder are radially polarized, and the first magnetic cylinder and the second magnetic cylinder are set to an angle of $>0°$ and $<90°$ between the N-S directions of two poles of the two magnetic cylinders; wherein the absorption medium is located between the first magnetic cylinder and the second magnetic cylinder.

In one embodiment of the present invention, the outer shell of the capsule has a circular cup-shaped structure, comprising a cup bottom, an annular wall extending from and perpendicular to the cup bottom, and an circular opening opposite to the cup bottom; and wherein a rotation limiting slot is cut in the annular wall close to the circular opening, which comprises an entrance part at a certain angle to the plane of the circular opening and a movement part parallel to the plane of the circular opening, and the entrance part is in connection with the movement part.

In another embodiment of the present invention, the inner shell of the capsule has a cap-shaped structure, comprising a cap top and an annular wall perpendicular to the cap top; and a rotation limiting pin is set near the junction of the cap top and the annular wall.

The present invention discloses a magnetically controlled digestive tract liquid collection system comprising an external magnet and a capsule, wherein the external magnet locates outside human body, and the capsule enters the digestive tract of the human body when used; and the capsule is described as set above.

DETAILED DESCRIPTION OF THE PREFERRED EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Figure 1:
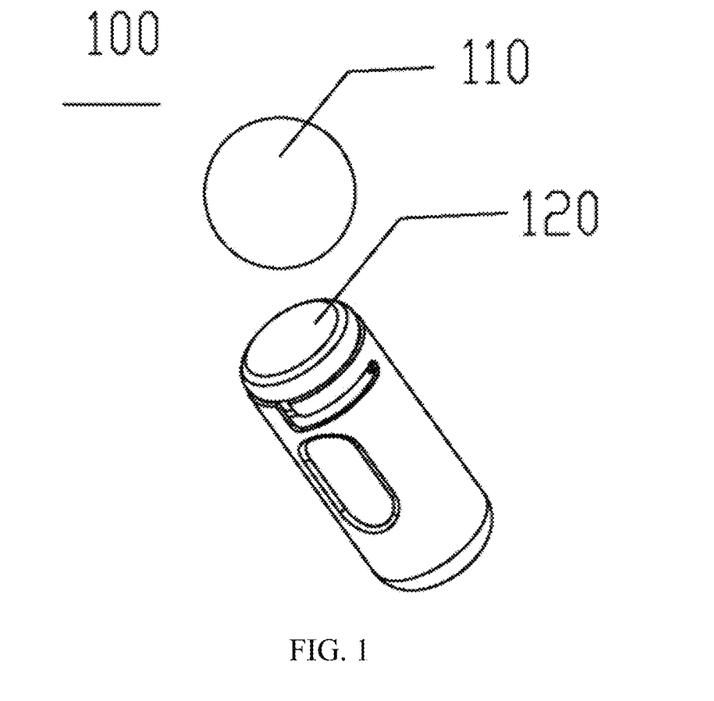
FIG. 1 shows a schematic illustration of a magnetically controlled digestive tract liquid collection system in accordance with the present invention.

Referring to FIG. 1, a magnetically controlled digestive tract liquid collection system 100 comprises an external magnet 110 and a capsule 120, wherein the capsule 120 is microstructured and enters human digestive tract through the mouth, and the external magnet 110 is located outside the human body.

Figure 2:
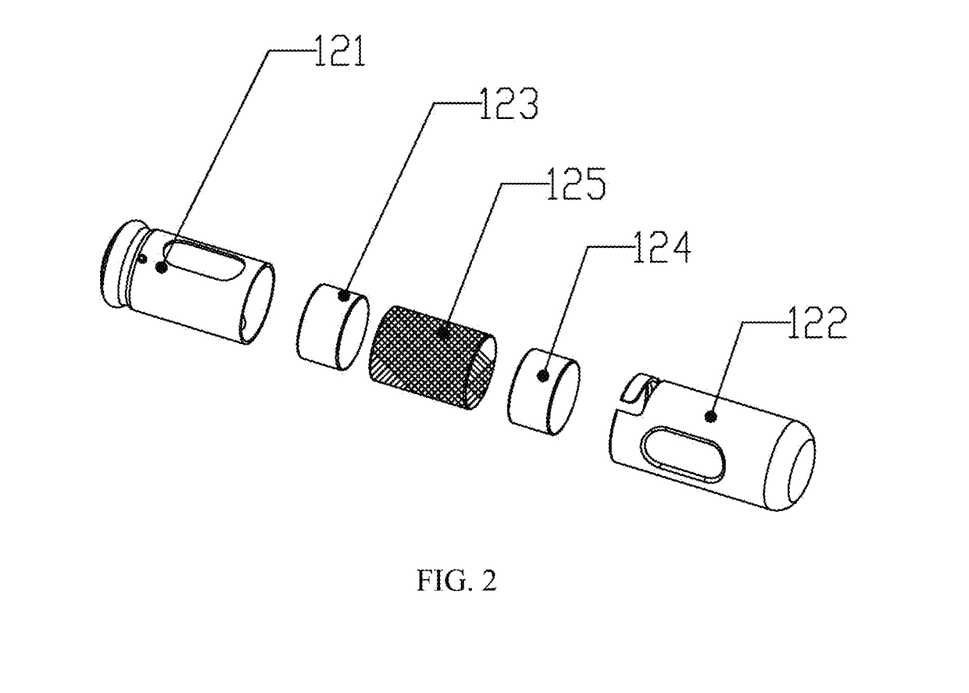
FIG. 2 shows an exploded view of a capsule shown in FIG. 1.

FIG. 2 shows the exploded view of the capsule 120. As shown in the figure, the capsule 120 comprises an inner shell 121, an outer shell 122, a first magnetic cylinder 123, a second magnetic cylinder 124 and an absorption medium 125, wherein the outer shell 122 is larger than the inner shell 121 in size. The inner shell 121 and the outer shell 122 are matched with each other and are latched by rotation to form an entire shell of the capsule 120. The first magnetic cylinder 123 is fixed in the inner shell 121, and the outer diameter of the first magnetic cylinder 123 is matched with the inner diameter of the inner shell 121. The second magnetic cylinder 124 is fixed in the outer shell 122, and the outer diameter of the second magnetic cylinder 124 is matched with the inner diameter of the outer shell 122. The first magnetic cylinder 123 and the second magnetic cylinder 124 are radially polarized, and the absorption medium 125 is located between the first magnetic cylinder 123 and the second magnetic cylinder 124.

The matching of the outer shell and the inner shell means that the outer shell has the same shape as the inner shell, can cooperate with each other and can be tightly coupled. In one embodiment, the outer shell and the inner shell are both in a hollow cylindrical shape, and the inner diameter of the outer shell is larger than the outer diameter of the inner shell a size from 0 to 0.02 mm.

The matching of the first magnetic cylinder and the inner shell means that the first magnetic cylinder and the inner shell are tight fit to an integration. In one embodiment, the first magnetic cylinder and the inner shell are fixed with glue to an integration.

The matching of the second magnetic cylinder and the outer shell means that the second magnetic cylinder and the outer shell are tight fit to an integration. In one embodiment, the second magnetic cylinder and the outer shell are fixed with glue to an integration.

Further rotationally sealed means that a seal is provided through rotation.

Figure 3:
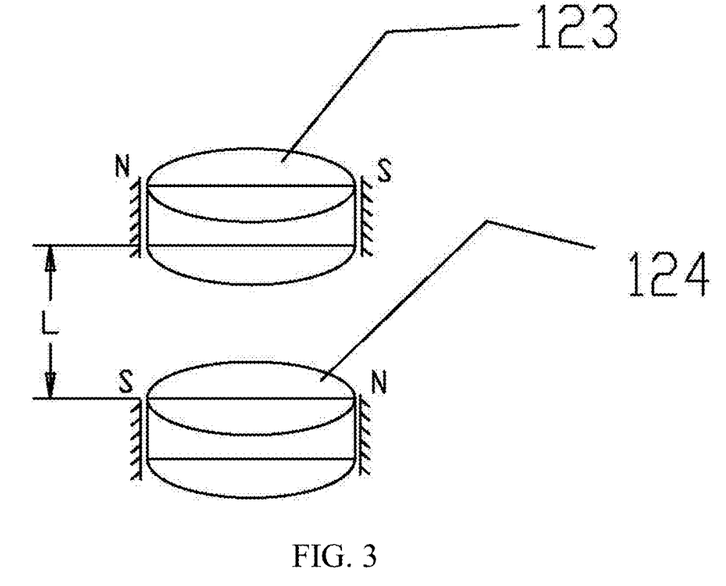
FIG. 3 shows a schematic illustration of two magnetic cylinders inside the capsule in a natural state without external force.

FIG. 3 shows a schematic illustration of the first magnetic cylinder 123 and the second magnetic cylinder 124 inside the capsule 120 in a natural state without external force. As shown in the figure, in a natural state without any external force, the first magnetic cylinder 123 and the second magnetic cylinder 124 are separated by a certain distance L, which is the thickness of the adsorption medium 125 sandwiched in the middle. In addition, the first magnetic cylinder 123 and the second magnetic cylinder 124 are radially polarized, and radial polarization means that the lines connecting N and S poles of the magnetic cylinders are aligned with the diameters. In one embodiment of the present invention, as shown in FIG. 3, in a natural state without any external force (including the external magnetic field or mechanical limit structure as described below), the first magnetic cylinder 123 and the second magnetic cylinder 124 have opposite N-S directions, while the two magnetic cylinders are parallel and coaxial, subject to radial constraint, and can rotate freely. When there are no external magnetic field and mechanical limit structure applied for rotation limiting, in the case of constant end of the two magnetic cylinders face spacing, a certain distance is kept between the two magnetic cylinders (the distance is the thickness of the adsorption medium 125), the N-S directions of the two magnetic cylinders are opposite, and the two magnetic cylinders are attracted by magnetic force. In an example, as shown in FIG. 3, the N pole of the first magnetic cylinder 123 is on the left side, and the S pole is on the right side; the N pole of the second magnetic cylinder 124 is on the right side, and the S pole is on the left side. Note that the N-S directions of the two magnetic cylinders in this case are opposite as shown in FIG. 3, that is, when no external force is applied, on the same side, the pole of one magnetic cylinder is N and the pole of the other is S, and vice versa.

In accordance with the present invention, the radial polarization of the first magnetic cylinder 123 and the second magnetic cylinder 124 is achieved by: first forming a desired shape of column with magnetic powder, then sintering, and finally magnetizing along the radial direction with an electromagnetic field. Generally, when a magnet is manufactured, the N and S poles of the magnet are determined according to the magnetic field applied.

Figure 4:
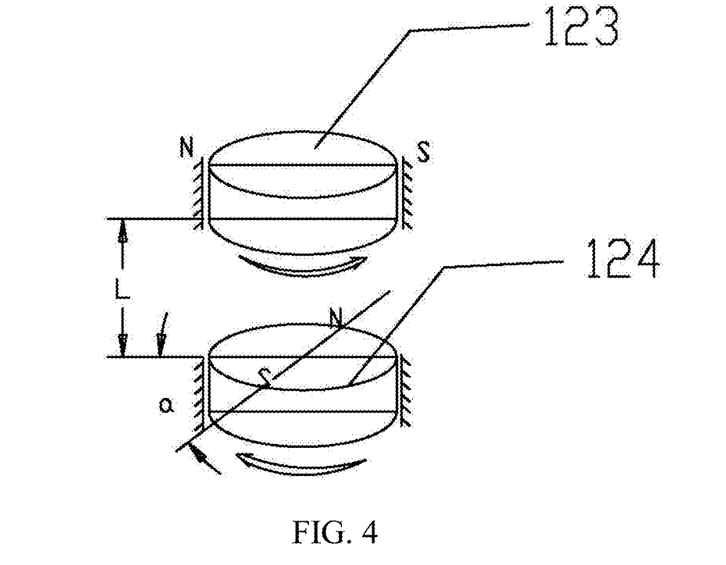
FIG. 4 shows a schematic illustration of two magnetic cylinders inside the capsule in a state, wherein an angle exists between the lines connecting two poles of the two magnetic cylinders.

FIG. 4 shows a schematic illustration of the first magnetic cylinder 123 and the second magnetic cylinder 124, wherein an angle exists between the lines connecting two poles of the two magnetic cylinders. Note that, with no external magnetic field, the angle is formed depending on the action of the limit structure as described below; when an external magnetic field is applied, both the external magnetic field and the limit structure can lead to this state. Moreover, in the state of use after assembly, an angle always exists between the lines connecting the N and S poles of the two magnetic cylinders. The angle α may be any one, provided that the two magnetic cylinders can rotate. In one embodiment of the present invention, the angle meets 0°<α<90°. In this case, at least one of the magnetic cylinders rotates relative to the other one, or both rotate relative to each other. Since there is a mutual attraction between the N pole of one magnetic cylinder and the S pole of the other one, or the S pole of one magnetic cylinder and the N pole of the other one, when the angle α is present, a torque can be generated between the two magnetic cylinders. Under the action of the torque, two magnetic cylinders will bind more tightly.

Figure 5:
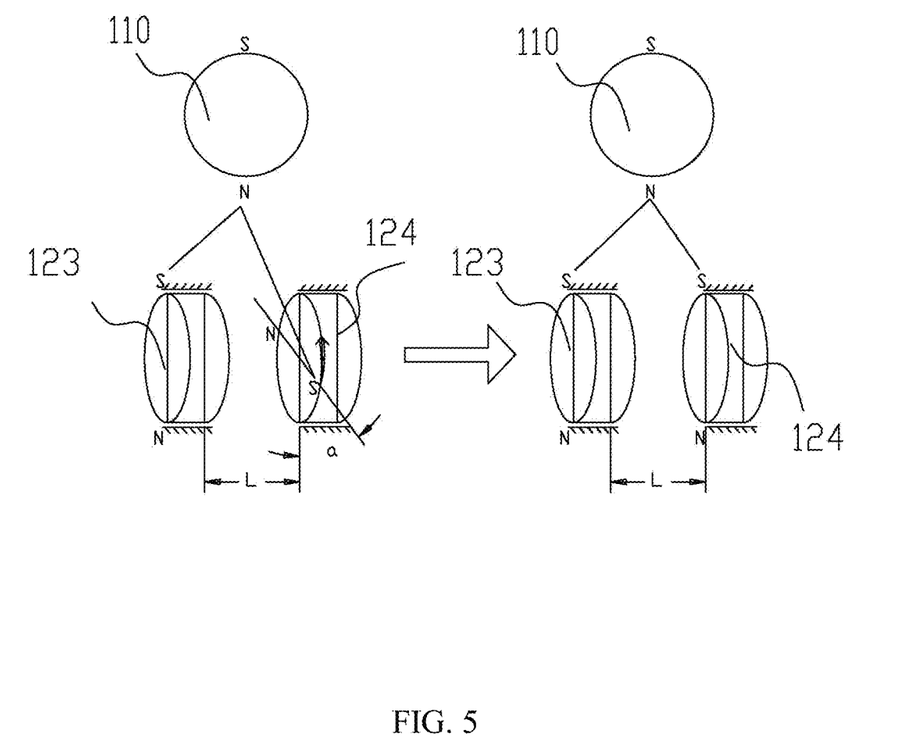
FIG. 5 shows a schematic illustration of two magnetic cylinders rotating when an external magnetic field is applied.

When an external magnetic field is applied, in an extreme case, the action of the external magnetic field makes the two magnetic cylinders same in N-S directions. That is, the external magnetic field enables N poles or S poles of the two magnetic cylinders to be at the same sides. In this case, the torque between the two magnetic cylinders is the biggest. In one embodiment of the present invention, as shown in FIG. 5, the first magnetic cylinder 123 and the second magnetic cylinder 124 are placed horizontally, and the left image shows a state when an external magnetic field is initially applied, wherein the initial angle α between the N-S directions of the first magnetic cylinder 123 and the second magnetic cylinder 124 is shown. The angle is limited by the limit structure described below. When the N pole of the external magnetic field approaches the first magnetic cylinder 123 and the second magnetic cylinder 124, the two magnetic cylinders can not move vertically away from or close to the external magnetic field as they are housed in the capsule 120, but at least one of the magnetic cylinders rotates instead. When the N pole of the external magnetic field gradually approaches the first magnetic cylinder 123 and the second magnetic cylinder 124, the S pole of the first magnetic cylinder 123 is attracted while the N pole of the second magnetic cylinder 124 is repelled. At this point, the second magnetic cylinder 124 can automatically rotate as it cannot move away from the external magnetic field in the vertical direction, so that the N pole of the magnetic cylinder moves away from the N pole of the external magnetic field, and the S pole of the magnetic cylinder approaches the N pole of the external magnetic field. Thus, the attraction of the external magnetic field to the first magnetic cylinder 123 and the second magnetic cylinder 124 gradually increases, so does the angle α between the two magnetic cylinders. As a result, the torque generated is also increased. In this case, the outer shell 122 is driven by the second magnetic cylinder 124 and the inner shell 121 is driven by the first magnetic cylinder 123. At least one or both of the two magnetic cylinders can rotate relative to the other one and the angle of rotation is consistent with the angle α. When the external magnetic field continues to infinitely approach the first magnetic cylinder 123 and the second magnetic cylinder 124, the N pole of the second magnetic cylinder 124 is deflected to the opposite side, and the first magnetic cylinder 123 and the second magnetic cylinder 124 are in the same direction, which the rotation torque generated between the two is the largest.

As the person having ordinary skill in the art can comprehend, in another embodiment of the present invention, when the S pole of the external magnetic field approaches the first magnetic cylinder 123 and the second magnetic cylinder 124, the S pole of the first magnetic cylinder 123 can repel it, making the first magnetic cylinder 123 rotate relative to the second magnetic cylinder 124. Since the first magnetic cylinder 123 is fixed in the inner shell 121, the rotation of the first magnetic cylinder 123 can drive the inner shell 121 to rotate relative to the outer shell 122. As the external magnetic field may approach from different directions, it is possible to make one or both of the two magnetic cylinders rotate. For example, in one embodiment of the present invention, when the external magnetic field approaches, at least one of the first magnetic cylinder 123 and the second magnetic cylinder 124 rotates relative to the other because of the repulsion of equal poles; in another embodiment of the present invention, when the external magnetic field approaches, both of the first magnetic cylinder 123 and the second magnetic cylinder 124 rotate. In either case, the result is that the first magnetic cylinder 123 and the second magnetic cylinder 124 rotates relative to each other, driving the inner shell 121 and the outer shell 122 to rotate relative to each other.

Figure 6:
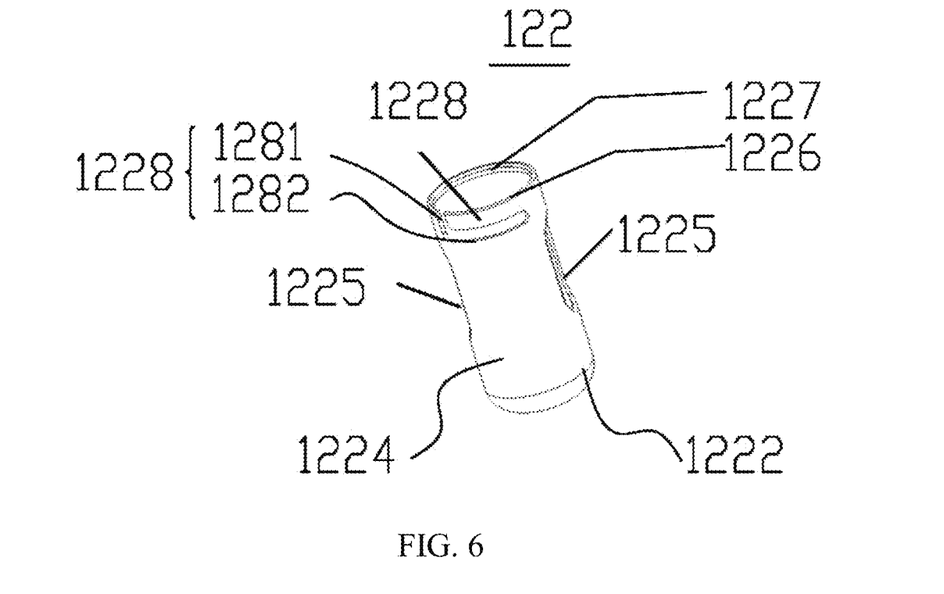
FIG. 6 shows a structural view of an outer shell of the capsule.

FIG. 6 shows a structural view of the outer shell 122. The outer shell 122 has a cup-shaped structure, comprising a cup bottom 1222, an annular wall 1224 extending from and perpendicular to the cup bottom 1222, and a circular opening 1226 opposite to the cup bottom 1222. Close to the circular opening 1226, a rotation limiting slot 1228 is cut in the annular wall 1224, which comprises an entrance part 1281 at a certain angle to the plane of the circular opening 1226 and a movement part 1282 parallel to the plane of the circular opening 1226, and the entrance part 1281 is in connection with the movement part 1282 to form a L-shaped slot. In one embodiment of the present invention, the entrance part 1281 is perpendicular to the movement part 1282. In another embodiment of the present invention, the entrance part 1281 is at an obtuse angle to the movement part 1282. In still another embodiment of the present invention, the entrance part 1281 is at an acute angle to the movement part 1282. Preferably, the junction between the entrance part 1281 and the movement 1282 is a smooth curved surface.

In one embodiment of the present invention, a liquid inlet is cut in the annular wall 1224, and the liquid inlet is in the vicinity of the entrance part 1281 of the rotation limiting slot 1228. In another embodiment of the present invention, two liquid inlets 1225 are cut in the annular wall 1224 at two sides of the rotation limiting slot 1228. Preferably, the two liquid inlets 1225 are located on the same axis of the annular wall 1224.

Figure 7:
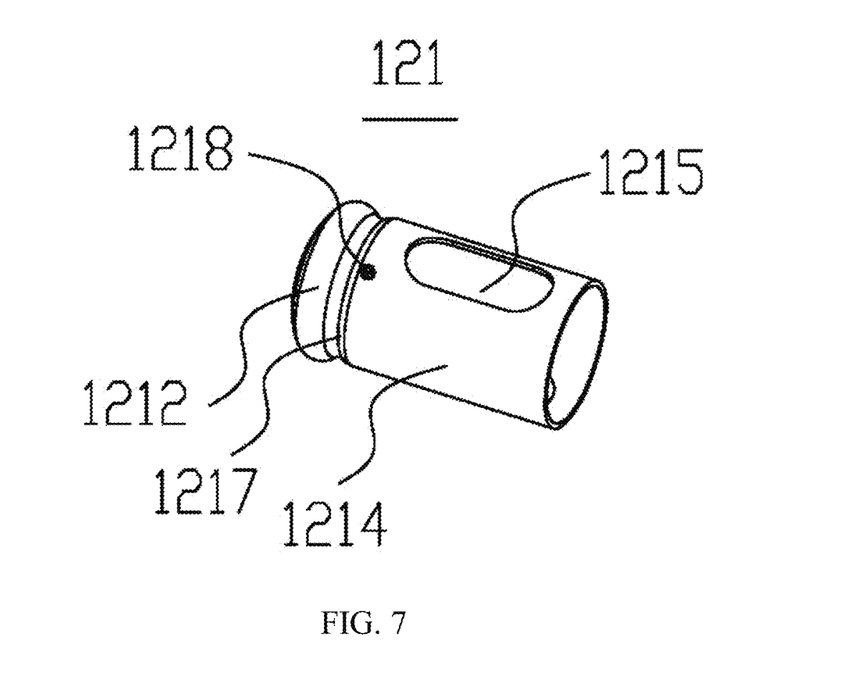
FIG. 7 shows a structural view of an inner shell of the capsule.

FIG. 7 shows a structural view of the inner shell 121. The inner shell 121 has a cap-shaped structure, comprising a cap top 1212 and an annular wall 1214 perpendicular to the cap top 1212. A rotation limiting pin 1218 is designed near the junction of the cap top 1212 and the annular wall 1214. The rotation limiting pin 1218 cooperates with the rotation limiting slot 1228 for rotationally engaging the inner shell 121 with the outer shell 122.

Before assembly, the N-S directions of the first magnetic cylinder 123 and the second magnetic cylinder 124 need to be measured by an instrument, and according to the directions measured, the first magnetic cylinder 123 is mounted in the inner shell 121, and the second magnetic cylinder 124 is mounted in the outer shell 122. To determine the mounting angles, the positions of the rotation limiting slot 1228 and the rotation limiting pin 1218 need to be considered. In the state of normal use where the external magnetic field is not applied, the rotation limiting slot 1228 and the rotation limiting pin 1218 form a limit structure which constrains the positions of the first magnetic cylinder 123 and the second magnetic cylinder 124, so that the angle α(0°<α<90°) exists between the N-S directions of the two magnetic cylinders. Presence of the angle α ensures an ever-present torque between the first magnetic cylinder 123 and the second magnetic cylinder 124 is always present, so that the entire structure is always in a tightened state. At the same time, there is always an attraction between the first magnetic cylinder 123 and the second magnetic cylinder 124. In this way, the magnetic cylinders can be unlikely to fall out of the capsule 120 in the digestive tract during use, thus meeting safety requirements.

To further enhance safety, in one embodiment of the present invention, internal threads 1227 are cut at the circular opening 1226 of the outer shell 122, and external threads 1217 are cut at the junction of the cap top 1212 and the annular wall 1214 of the inner shell 121. The external threads 1217 fit the internal threads 1227, and the external threads 1217 and the internal threads 1227 are on a threaded connection. As thus, even in a special case where the rotation limiting pin 1218 on the inner shell 121 is rotated to the entrance part 1281, but there is still a risk of falling off on account of gastrointestinal peristalsis or external force, safety in use of the capsule 120 can be ensured depending on the threaded connection between the external threads 1217 and the internal threads 1227.

In addition, in one embodiment of the present invention, a liquid inlet 1215 is cut in the annular wall 1214 of the inner shell 121, in the vicinity of the rotation limiting pin 1218. In another embodiment of the present invention, two liquid inlets 1215 are cut in the annular wall 1214 of the inner shell 121, one of which is located near the rotation limiting pin 1218, and the two are symmetric with respect to the central axis of the capsule 120. Preferably, the two liquid inlets 1215 are located on the same axis of the annular wall 1214.

So, when no magnetic field is applied, the plane formed by the liquid inlet 1215 near the rotation limiting pin 1218 of the inner shell 121 and the central axis of the capsule 120 is in the first direction; the plane formed the liquid inlet 1225 near the rotation limiting slot 1228 of the outer shell 122 and the central axis of the capsule 120 is in the second direction. The first direction is at an angle to the second direction. Preferably, the angle is 90°, referring to FIG. 2, FIG. 6, and FIG. 7.

It should be noted that the set positions of the rotation limiting slot 1228, the rotation limiting pin 1218 and the liquid inlets as set forth are good for implementation of the invention for liquid collection. In one embodiment of the present invention, each of the inner shell 121 and the outer shell 122 is designed with one liquid inlet. The directions of planes formed by the two liquid inlets and the central axis of the capsule 120 are perpendicular to each other, and the two liquid inlets are adjacent to each other. When there is no external magnetic field, the two liquid inlets are covered mutually, making the capsule 120 closed; when an external magnetic field is applied, the two liquid inlets reach an alignment by rotation of the outer and inner shells, making the capsule 120 opened for liquid collection.

In another embodiment of the prevent invention, each of the inner shell 121 and the outer shell 122 is designed with two liquid inlets. In the case of no external magnetic field, the first direction where the two liquid inlets 1215 of the inner shell 121 are in is at an angle to the second direction where the two liquid inlets 1225 of the outer shell 122 are in. Preferably, the angle is 90°. But it is only necessary to ensure that all of the liquid inlets of the capsule 120 are closed when no external magnetic field is applied. When an external magnetic field is applied, under the action of magnetic field, the inner shell 121 and the outer shell 122 rotate relative to each other, turning the two liquid inlets 1215 of the inner shell 121 and the two liquid inlets 1225 of the outer shell 122 to an open state. As thus, the digestive liquid in the digestive tract can be collected for sampling. To achieve the above technical effects, in one embodiment of the present invention, the N-S direction of the first magnetic cylinder 123 is the same as the axial direction of the liquid inlet 1215 of the inner shell 121 during installation, that is, the N-S direction of the first magnetic cylinder 123 passes through the liquid inlet 1215 of the inner shell 121. The N-S direction of the second magnetic cylinder 124 needs to be perpendicular to the axial direction of the liquid inlet 1225 of the outer shell 122. In another embodiment of the present invention, during installation, the N-S direction of the first magnetic cylinder 123 is perpendicular to the axial direction of the liquid inlet 1215 of the inner shell 121, while the N-S direction of the second magnetic cylinder 124 is parallel to the axial direction of the liquid inlet 1225 of the outer shell 122. That is, when the external magnetic field is not applied, the N-S directions of the first magnetic cylinder 123 and the second magnetic cylinder 124 are opposite, but both are in the same axial direction; and the axial direction of the two liquid inlets 1215 of the inner shell 121 is at an angle to the axial direction of the two liquid inlets 1225 of the outer shell 122. Preferably, the angle is 90°. In this case, after assembly, when the external magnetic field is not applied, the two liquid inlets 1215 and the two liquid inlets 1225 are covered up by the outer shell 122 and the inner shell 121 as an angle exists between axial directions of the liquid inlets, even a 90°, thereby making the whole capsule 120 closed.

Figure 8:
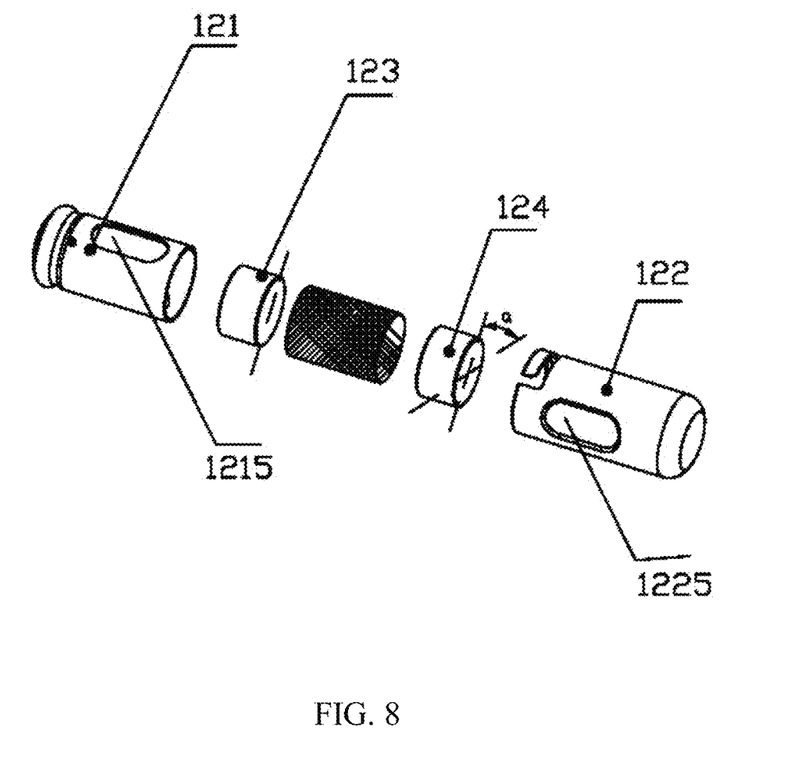
FIG. 8 shows an exploded view of the capsule when an external magnetic field is applied.

FIG. 8 shows an exploded view of the capsule 120 when an external magnetic field is applied. As shown in the figure, the first magnetic cylinder 123 is integrally mounted in the inner shell 121, the second magnetic cylinder 124 is integrally mounted in the outer shell 122, and the adsorption medium 125 is sandwiched between the first magnetic cylinder 123 and the second magnetic cylinder 124. When an external magnetic field is applied, such as in the embodiment shown in FIG. 8, the second magnetic cylinder 124 rotates along the central axis of the capsule 120 because of the action of magnetic force, driving the outer shell 122 to rotate. As thus, the liquid inlets 1215 and 1225 covered up by the shells will come out as the inner shell 121 and the outer shell 122 rotate relative to each other to make the capsule 120 open for liquid collection.

In one embodiment of the present invention, the liquid inlets 1215 and 1225 can be various shapes and sizes, for example, elliptical, rectangular, square, trapezoidal, star, triangular, etc., and the widths thereof are positively correlated with the angle α. The requirements of the present invention can be met, provided the shapes of the liquid inlets 1215, 1225 allow them to be closed and opened during rotation.

In one embodiment of the present invention, the external magnetic field may be either a magnetic ball or a magnetic cylinder, not limited to a column.

Figure 9:
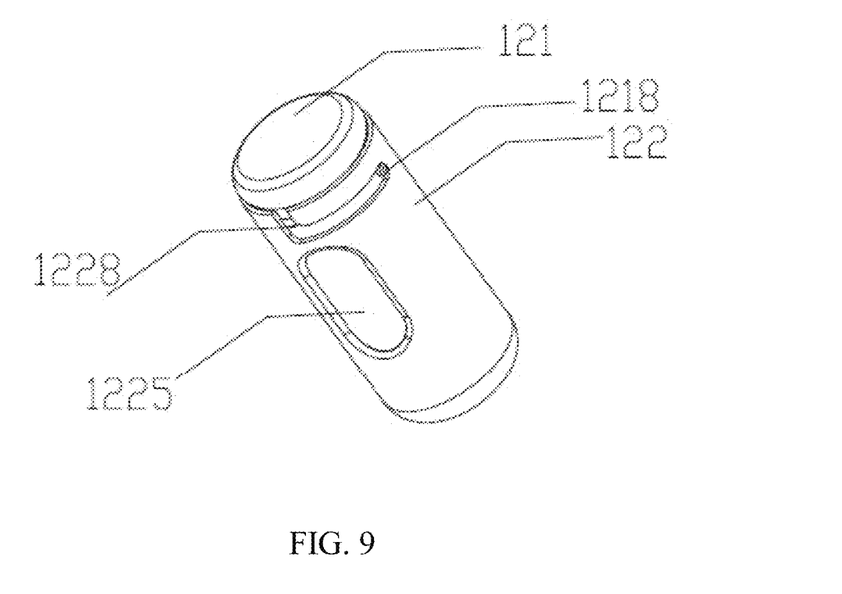
FIG. 9 shows an assembled view of the capsule.

FIG. 9 shows an assembled view of the capsule 120. After assembly, the rotation limiting pin 1218 and the rotation limiting slot 1228 fitting each other form a limit structure which provides a number of functions, including: guide the relative rotation of the inner shell 121 or the outer shell 122; combine the capsule 120 firmly for not spitting in use; maintain an angle between the N-S directions of the first magnetic cylinder 123 and the second magnetic cylinder 124, which produces an always existing torque between the two magnetic cylinders and thereby enhances the mutual joining force of the inner shell 121 and the outer shell 122.

In a word, the limit structure formed by the rotation limiting pin 1218 and the rotation limiting slot 1228 together is intended for guiding and limiting purposes in relative rotation of the inner shell 121 and the outer shell 122. Those skilled in the art can understand that the limit structure is not limited to the rotation limiting slot, the rotation limiting pin, and may be other forms. For example, in one embodiment of the invention, the limit structure is a combination of bump and slide rail.

Figure 10:
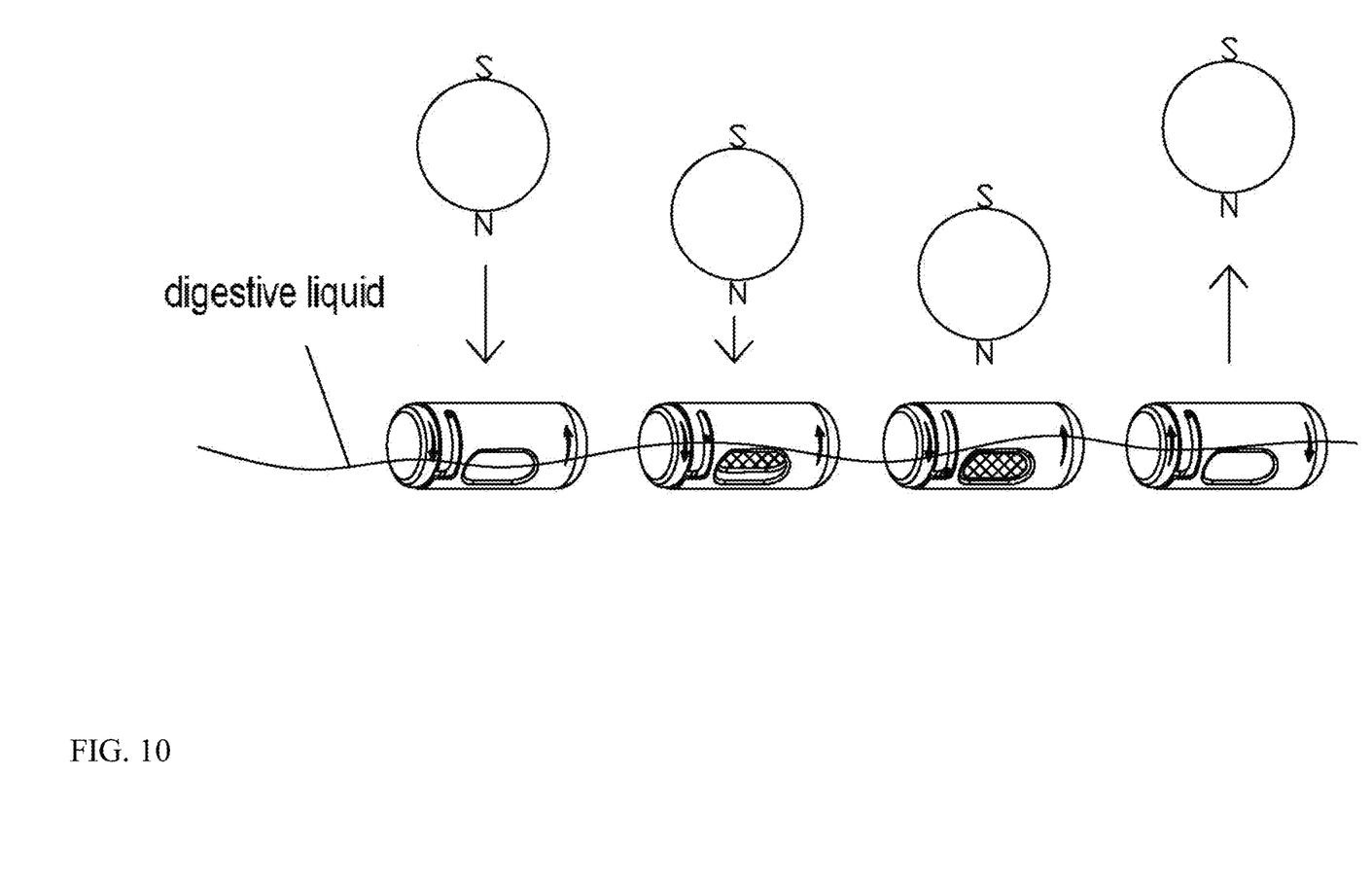
FIG. 10 shows a schematic illustration of the magnetically controlled digestive tract liquid collection system in service.

Referring to FIG. 10, a schematic illustration of the magnetically controlled digestive tract liquid collection system 100 in service, the capsule 120 is floating in a digestive liquid. When the external magnetic field is not applied, the liquid inlets of the capsule 120 are closed; when the external magnetic field is applied, magnetic force begins to act on the magnetic cylinders in the capsule 120, and as the external magnetic field approaches the capsule 120, the liquid inlets begin to open gradually until fully opened, reaching the maximum efficiency in liquid collection. If the external magnetic field is removed, the capsule 120 returns to the state where liquid inlets are closed.

Figure 11:
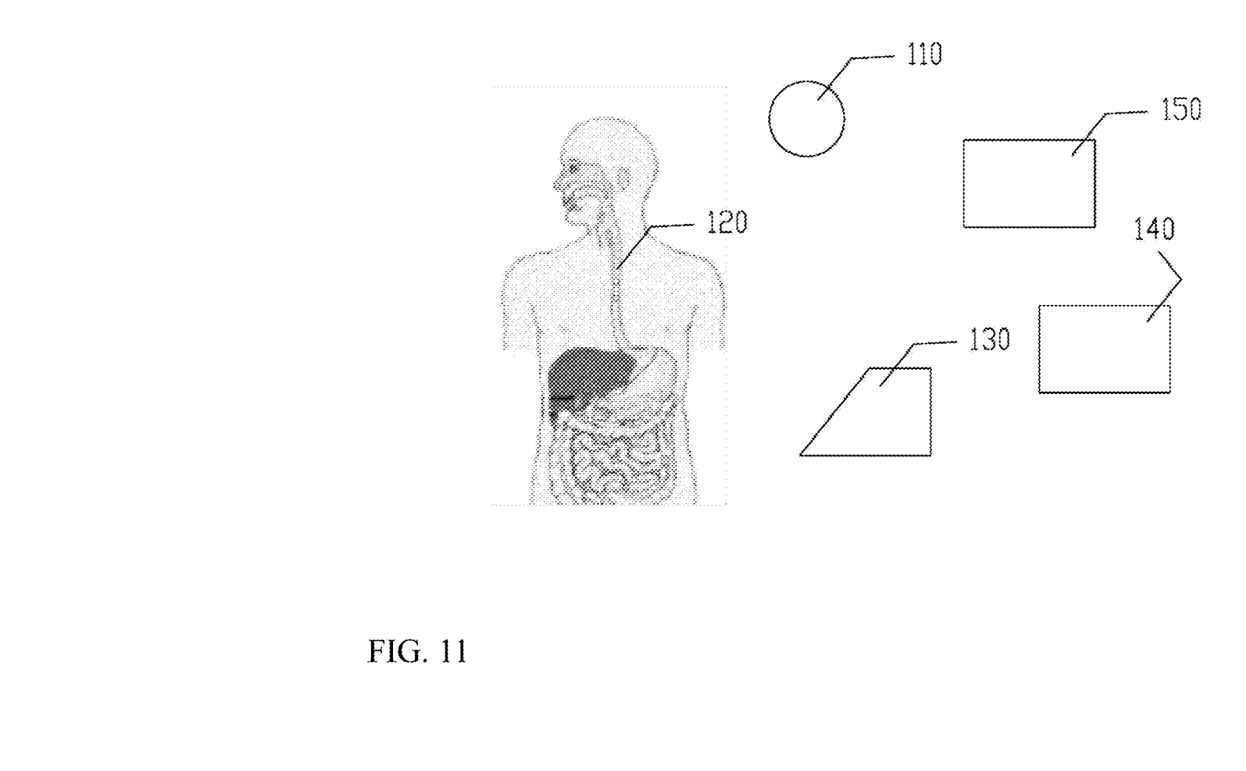
FIG. 11 shows an overall structural view of the magnetically controlled digestive tract liquid collection system.

In practical application, it is necessary to first detect the preset position of the capsule 120 in the human body, and then apply an external magnetic field to control the capsule to collect liquid. In order to determine the position of the capsule 120 in the digestive tract (GI tract), as shown in FIG. 11, the magnetically controlled digestive tract liquid collection system 100 disclosed herein further comprises a position detection unit 130 and a wireless communication unit 140 between which there is a communication of signals. The position detection unit 130 is configured in the capsule 120 for detecting position information of the capsule 120, and the wireless communication unit 140 is configured to receive the position information transmitted from the position detection unit 130, and send the information to an external device

150. The external device 150 is designed with an image display from which the operator or the external control device can obtain the position information of the capsule 120 in human body to determine whether or not to apply an external magnetic field. In one embodiment of the present invention, the external device is a computer with an image display function. In one embodiment of the present invention, the external control device may be a smart device such as a computer, a tablet computer, or a mobile phone that can give control commands.

The methods for detecting the position information of the capsule 120 include but not limited to the followings:

In one embodiment of the present invention, the position detection unit 130 comprises a timer and a data transmitting and receiving unit. A liquid collection time is preset in the timer, which may be an average value summarized by the medical institution, or the value obtained in previous liquid collection, or the average value summarized according to the time values of multiple liquid collections. Based on a running time collected by the timer and the preset liquid collection time, whether or not the capsule 120 has reached an expected position is determined. The data transmitting and receiving unit is configured for data transmission with the wireless communication unit 140. In the preferred embodiment, the timer calculates the running time of the capsule 120 in the digestive tract, and compares the running time with the preset liquid collection time, and when the running time reaches the preset liquid collection value (that is, running time reset liquid collection value), it is determined that the capsule 120 has reached the expected position; the data transmitting and receiving unit transmits the information that the capsule has reached the expected position to the external device 150 via the wireless communication unit 140. Then, the operator or external control device can decide whether or not to apply an external magnetic field.

In another embodiment of the present invention, the position detection unit 130 is a pH sensor. The pH sensor can select the pH ranges according to the desired regions to be detected. In an example, the pH sensor can accurately detect the pH values in ranges 2-12, 4-8, or 7.6-8. According to the existing medical experience, the human stomach is acidic while the duodenum is alkaline. Therefore, by means of the pH value detected, it can be determined whether the capsule 120 is in the stomach or the intestine. The pH in colon is around 7.8, so the pH sensor using the pH detection range of 7.6-8 can effectively detect whether the capsule is in the colon.

In another embodiment of the present invention, the position detection unit 130 employs a magnetic field tracking method to detect the position of the capsule 120. The position detection unit 130 comprises a number of magnetic dipole units which are configured along the digestive tract of human body. The magnetic dipole unit may be a magnetic dipole moment having a current density of 0.1 A/cm^2 to 1 A/cm^2 and a weight of 0.5 g-5 g. The magnetic dipole units input movement positions of the capsule 120 into a preset digestive tract diagram, and the position of the capsule 120 in the digestive tract is determined according to the preset digestive tract diagram.

In still another embodiment of the present invention, the position detection unit 130 comprises an external sensing unit placed near the ileocecal valve of patient to detect whether the capsule is in the colon. Once the capsule 120 enters the colon, the unit can detect a signal and thereby determine the exact entry time. Several detection methods are available for the external sensing unit, including but not limited to: body surface magnetic field detection, radio frequency (RF) detection, or ultrasonic sensing.

In still another embodiment of the present invention, the position detection unit 130 is an enzyme sensor located outside the capsule 120. In an example, the unit is an enzyme sensor located on the outer shell 122. The enzyme sensor is used to detect whether or not enzyme exists in the regions of digestive tract, such as an enzyme sensor specifically for detecting the presence of enzyme in colon. If enzyme is detected in colon, the enzyme sensor sends a signal to the external device 150 through the wireless communication unit 140 to confirm that the capsule 120 has reached the colon.

In still another embodiment of the present invention, the position detection unit 130 comprises a number of external sensors which are configured along the digestive tract of human body. The external sensing device can be, but not limited to, a magnet, an RF unit, or an ultrasonic sensing unit. When the capsule 120 is moving in the digestive tract, one of the external sensors, closest to the capsule 120, senses the strongest signal, and thereby the position of the capsule 120 is determined.

In accordance with the methods described above, after the position detection unit 130 determines that the capsule 120 has reached the expected position, the operator or external control device applies an external magnetic field to the capsule 120, controlling the liquid inlets to open and close for liquid collection.

In summary, in the magnetically-controlled digestive tract liquid collection system disclosed herein, the first magnetic cylinder 123 is embedded in the inner shell 121 of the capsule 120 and the second magnetic cylinder 124 is embedded in the outer shell 122 of the capsule 120. An external magnetic field may act to cause the first magnetic cylinder 123 or the second magnetic cylinder 124 to rotate relatively, forming an angle $\alpha$ between the N-S directions, and thereby producing a torque between the two magnetic cylinders. The relative rotation of the two magnetic cylinders is constrained by the rotation limiting slot 1228 and the rotation limiting pin 1218 in the process of applying or withdrawing of the external magnetic field. In another aspect of the invention, rotation between the magnetic cylinders 123 and 124 drives the inner shell 121 and the outer shell 122 to rotate relatively, causing the liquid inlets 1215 and 1225 thereon to be misaligned, and thereby making the liquid inlets 1215 and 1225 closed or opened depending on whether an external magnetic field is applied or not. In addition, there is mutual attraction between the first magnetic cylinder 123 and the second magnetic cylinder 124, which can firmly combine the inner shell 121 and the outer shell 122 and ensure no separation along the axial direction of the capsule 120.

Optionally, internal threads 1227 are cut at the circular opening 1226 of the outer shell 122 and external threads 1217 are cut at corresponding position of the inner shell 121. The threaded connection further ensures that the inner shell 121 and the outer shell 122 can not separate along the axial direction of the capsule 120.

Based on the design described above, the structure of the capsule 120 is simplified, and when the size of the capsule is constant, the volume occupied by the adsorption medium can be larger, so that more digestive liquid can be adsorbed at sampling, and the capsule capacity is thereby increased.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A capsule, comprising an inner shell, an outer shell, a first magnetic cylinder, a second magnetic cylinder and an absorption medium, wherein the outer shell is larger than the inner shell, and the outer shell and the inner shell are matched with each other and are rotationally sealed;

the first magnetic cylinder is fixed in the inner shell, and the outer diameter of the first magnetic cylinder is matched with the inner diameter of the inner shell;

the second magnetic cylinder is fixed in the outer shell, and the outer diameter of the second magnetic cylinder is matched with the inner diameter of the outer shell;

the first magnetic cylinder and the second magnetic cylinder are radially polarized, and the first magnetic cylinder and the second magnetic cylinder are set to an angle of >0° and <90° between the N-S directions of two poles of the two magnetic cylinders;

the absorption medium is located between the first magnetic cylinder and the second magnetic cylinder.

2. The capsule of claim 1, wherein when no external magnetic field is applied, the angle between the N-S directions of two poles of the first magnetic cylinder and the second magnetic cylinder is >0° and <90° and the two magnetic cylinders are attracted to each other; and when an external magnetic field is applied, at least one of the first magnetic cylinder and the second magnetic cylinder rotates along central axis of the capsule to drive the inner shell and the outer shell to rotate together.

3. The capsule of claim 1, wherein the outer shell of the capsule has a circular cup-shaped structure, comprising a cup bottom, an annular wall extending from and perpendicular to the cup bottom, and an circular opening opposite to the cup bottom; and wherein a rotation limiting slot is cut in the annular wall close to the circular opening, which comprises an entrance part at a certain angle to the plane of the circular opening and a movement part parallel to the plane of the circular opening, and the entrance part is in connection with the movement part.

4. The capsule of claim 3, wherein a liquid inlet is cut in the annular wall of the outer shell, in the vicinity of the entrance part of the rotation limiting slot.

5. The capsule of claim 3, wherein two liquid inlets are cut in the annular wall of the outer shell at two sides of the rotation limiting slot.

6. The capsule of claim 3, wherein the circular opening of the outer shell is designed with internal threads.

7. The capsule of claim 1, wherein the inner shell of the capsule has a cap-shaped structure, comprising a cap top and an annular wall perpendicular to the cap top; and a rotation limiting pin is set near the junction of the cap top and the annular wall.

8. The capsule of claim 7, wherein a liquid inlet is cut in the annular wall of the inner shell, in the vicinity of the rotation limiting pin.

9. The capsule of claim 7, wherein two liquid inlets are cut in the annular wall of the inner shell, which one liquid inlet is in the vicinity of the rotation limiting pin and another liquid inlet is set symmetrical about the central axis of the capsule.

10. The capsule of claim 7, wherein external threads are cut around the junction of the cap top and the annular wall of the inner shell.

11. A magnetically controlled digestive tract liquid collection system, comprising an external magnet and a capsule, wherein the external magnet locates outside human body, and the capsule enters the digestive tract of the human body when used;

wherein the capsule comprising an inner shell, an outer shell, a first magnetic cylinder, a second magnetic cylinder and an absorption medium, wherein the outer shell is larger than the inner shell, and the outer shell and the inner shell are matched with each other and are rotationally sealed;

the first magnetic cylinder is fixed in the inner shell, and the outer diameter of the first magnetic cylinder is matched with the inner diameter of the inner shell;

the second magnetic cylinder is fixed in the outer shell, and the outer diameter of the second magnetic cylinder is matched with the inner diameter of the outer shell;

the first magnetic cylinder and the second magnetic cylinder are radially polarized, and the first magnetic cylinder and the second magnetic cylinder are set to an angle of >0° and <90° between the N-S directions of two poles of the two magnetic cylinders;

the absorption medium is located between the first magnetic cylinder and the second magnetic cylinder.

12. The magnetically controlled digestive tract liquid collection system of claim 11, further comprising a position detection unit and a wireless communication unit, wherein the wireless communication unit communicates with the position detection unit; the position detection unit is in the capsule for detecting position information of the capsule; and the wireless communication unit receives the position information transmitted from the position detection unit, and sends the position information to an external device.

13. The magnetically controlled digestive tract liquid collection system of claim 12, wherein the position detection unit comprises a timer and a data transmitting and receiving unit; a liquid collection time is preset in the timer, whether the capsule has reached an expected position or not is determined based on the preset liquid collection time; the data transmitting and receiving unit sends the position information to the wireless communication unit when the capsule reaches the expected position.

14. The magnetically controlled digestive tract liquid collection system of claim 12, wherein the position detection unit is a pH sensor which determines the position of the capsule according to pH value of the liquid collected.

15. The magnetically controlled digestive tract liquid collection system of claim 11, further comprising a position detection unit is an external sensing unit for placement within sensing distance to the ileocecal valve of the human body to detect whether the capsule is in the colon.

16. The magnetically controlled digestive tract liquid collection system of claim 12, wherein the position detection unit is an enzyme sensor located outside the capsule for detecting whether or not enzyme exists in the regions of digestive tract.

17. The magnetically controlled digestive tract liquid collection system of claim 12, wherein the position detection unit comprises a plurality of external sensors which are configured along the digestive tract of human body; one of the external sensors which is closest to the capsule senses the strongest signal when the capsule is moving in the digestive tract, and the position of the capsule is determined based on the strongest signal.

18. The magnetically controlled digestive tract liquid collection system of claim 12, wherein the position detection unit comprises a plurality of magnetic dipole units which are configured along the digestive tract of human body; the magnetic dipole units input movement positions of the capsule into a preset digestive tract diagram, and the position of the capsule in the digestive tract is determined according to the digestive tract diagram.

* * * * *